(12) United States Patent
Carpena et al.

(10) Patent No.: US 6,338,810 B1
(45) Date of Patent: Jan. 15, 2002

(54) METHOD FOR MAKING APATITE CERAMICS, IN PARTICULAR FOR BIOLOGICAL USE

(75) Inventors: Joëlle Carpena, Jouques; Benoît Donazzon, Lanta; Jean-Louis Lacout, Toulouse; Michèle Freche, Fonsegrives, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/582,076
(22) PCT Filed: Dec. 22, 1998
(86) PCT No.: PCT/FR98/02827
 § 371 Date: Aug. 3, 2000
 § 102(e) Date: Aug. 3, 2000
(87) PCT Pub. No.: WO99/33766
 PCT Pub. Date: Jul. 8, 1999

(30) Foreign Application Priority Data

Dec. 23, 1997 (FR) .............................. 97/16357

(51) Int. Cl.$^7$ .............................. A61C 13/00; B05D 3/00
(52) U.S. Cl. .......................... 264/16; 264/19; 264/234; 264/667; 427/2.27
(58) Field of Search ........................... 264/16, 19, 667, 264/234; 427/2.27

(56) References Cited

U.S. PATENT DOCUMENTS 4,871,578 A * 10/1989 Adam et al. .................. 427/2
4,960,646 A * 10/1990 Shimamune et al. ........ 428/471
5,958,504 A * 9/1999 Lee et al. ................... 427/2.24
6,206,957 B1 * 3/2001 Driessens et al. ............. 106/35

FOREIGN PATENT DOCUMENTS

EP 0548365 6/1993

OTHER PUBLICATIONS

N. Yamasaki, et al. "Porous Hydroxyapatite Ceramics Prepared By Hydrothermal Hot–Pressing," Journal of Materials Science Letters, vol. 9, No. 10, Oct. 1, 1990, pp. 1150–1151.

S. Raynaod, et al., "Mechanical Fatigue Of Hot Pressed Hydroxyapatite" Bioceramics, vol. 10, Edited by L. Sedel and C. Roy , Proceedings of the 10$^{th}$ International Symposium on Ceramics in Medicine, 1997 Elsevier Science Ltd.

* cited by examiner

*Primary Examiner*—Christopher A. Fiorilla
(74) *Attorney, Agent, or Firm*—Burns Doane Swecker & Mathis LLP

(57) ABSTRACT

A process for manufacturing an apatite ceramic, especially for biological use involves the preparation of a homogeneous mixture of powders to form a hydroxyapatite of formula $Ca_{10}(PO_4)_6(OH)_2$, stoichiometric or non-stoichiometric, possibly containing other additives or flaws, compacting the mixture under a pressure of 100 to 500 Mpa at room temperature, and subjecting it to hydrothermal treatment at low temperature (100 to 500° C.) in the presence of water and in a sealed chamber.

20 Claims, 1 Drawing Sheet

METHOD FOR MAKING APATITE CERAMICS, IN PARTICULAR FOR BIOLOGICAL USE

This application is 371 of PCT/FR98/02827 filed Dec. 12, 1998.

DESCRIPTION

1. Field of the invention

The present invention involves a process for manufacturing an apatite ceramic, usable in particular for making apatites for biological use.

Apatites are very useful materials for many applications, for example in agriculture as a fertiliser, in orthopaedics as a biomaterial and in analytic chemistry as a chromatographic support.

The apatites have the general formula:

$$Me_{10}(XO_4)_6Y_2 \quad (I)$$

in which Me is one or several cations, $XO_4$ represents $PO_4$, and/or other anionic groups, and Y represents one or several anions such as OH, Cl and F. Among these apatites, phosphocalcic hydroxyapatite:

$$Ca_{10}(PO_4)_6(OH)_2 \quad (II)$$

is the best known compound.

The apatites of formula (I) can have various substitutions, for the cationic sites (Me) as well as for the anionic sites ($XO_4$ and/or $Y_2$).

Depending on the various uses planned, these substitution possibilities can be used to improve the physical and/or chemical properties of these apatites.

Apatites, particularly those of formula (II), can be non-stoichiometric, i.e. having a calcium/phosphorous atomic ratio different from that of the stoichiometric apatite of formula (II) which is 1.677.

In the non-stoichiometric apatites, this ratio is generally less than 1.677. This non-stoichiometry is explained in particular by the presence of flaws in the cationic/calcium sites, and/or by the presence of $HPO_4^{2-}$ ions substituting for phosphate ions. A general formula for the apatites could be given as:

$$Ca_{10-x}V_x(PO_4)_{6-y}(HPO_4)_y(OH)_{2+y-2x} \quad (III)$$

in which V represents a flaw and in which x and y are such that x<1, y<1, and y·x. When x=y=0, the apatite is stoichiometric.

Among the apatites, there are known non-stoichiometric biological apatites which form the mineral part of hard tissues, teeth and bones.

The use of apatites in biological areas, orthopaedics or dentistry is due to their perfect biocompatibility. This biocompatibility is attributed to the structure and composition of hydroxyapatite which are very close to those of the mineral part of calcified tissues. Most calcium orthophosphates including tricalcium phosphate, dicalcium phosphate and octocalcium phosphate also have excellent biocompatibility properties. Hydroxyapatites and more generally calcium orthophosphates are recognised as having osteoconduction properties.

With regard to solubility, hydroxyapatites have low solubility in biological media while other calcium orthophosphates are much more soluble, as can be seen in the appended table which gives the solubilities of these various phosphates.

There are many biological uses for apatites. They can be used for filling (in the form of powder or granulates), covering (in the form of powder projected by plasma projection) or in the form of massive pieces for resistant fillings or fixing: osteotomy wedges, screws, interstomatic frames, etc. For the latter uses, the apatite must be prepared in the form of a massive piece.

2. State of the Prior Art

Until now, massive pieces in apatite were prepared from powdered apatites subjected to sintering at high temperatures (greater than 1000° C.) with or without pressure.

The document Bioceramics, Vol. 10, 1997, pages 75 to 78, illustrates the densification of polycrystalline hydroxyapatite by hot compression at 1165° C. under 10 MPa.

The process currently used for preparation of hydroxyapatite biomaterials thus requires prior preparation of apatite power, putting it into granular form and sintering it at a high temperatures, according to various process such as natural sintering, pressure-assisted sintering, and sintering after using slip.

These techniques yield mass pieces with good mechanical properties, but they require high-temperature thermal treatments involving:

high costs of energy for preparation of the apatite partial transformation of hydroxyapatite to oxyapatite, and difficulties in enclosing species which are volatile or degradable at the temperature of the thermal treatment in the piece of apatite.

BRIEF DESCRIPTION OF THE INVENTION

This invention precisely involves a process for making apatite ceramics which produces pieces with good mechanical properties but without the need for thermal treatment at high temperatures.

According to the invention, the process for manufacturing of an apatite ceramic involves the following steps:

a) preparing a homogeneous mixture of powders including at least two calcium phosphates chosen from: $Ca(H_2PO_4)_2$, $Ca(H_2PO_4)_2 \cdot H_2O$, $Ca(HPO_4)$, $Ca(HPO_4) \cdot 2H_2O$, $Ca_3(PO_4)_2$, • or • variety, and $Ca_4(PO_4)_2O$, in quantities such that the mixture corresponds to a hydroxyapatite of formula:

$$Ca_{10}(PO_4)_6(OH)_2 \quad (II)$$

having a Ca/P atomic ratio equal to 1.667 or a non-stoichiometric hydroxyapatite of formula:

$$Ca_{10-x}V_x(PO_4)_{6-y}(HPO_4)_y(OH)_{2+y-2x} \quad (III)$$

in which V represents a flaw and in which x and y are such that x<1, y<1, and y·x, having a Ca/P atomic ratio less than 1.667.

b) compacting the mixture of powders obtained in step a) at room temperature, under a pressure of 100 to 500 MPa, to yield a compacted piece; and c) subjecting the compacted piece to hydrothermal treatment in a sealed chamber containing an aqueous medium, at a temperature of 100 to 500° C., for a period of at least 8 hours.

The process described above yields a stoichiometric or non-stoichiometric hydroxyapatite, at low temperature, because the temperature used in the last step does not exceed 500° C., thus offering many advantages in terms of energy costs and the possibility of enclosing species which are volatile or unstable at temperatures greater than 500° C. in the hydroxyapatite. The massive pieces obtained have good mechanical properties and can be easily machined.

The invention process can also be used to make stoichiometric apatite ceramics with the formula:

$$Ca_{10}(PO_4)_6(OH)_2 \quad (II)$$

or non-stoichiometric apatite ceramics with the formula:

$$Ca_{10-x}V_x(PO_4)_{6-y}(HPO_4)_y(OH)_{2+y-2x} \quad (III)$$

in which V represents a flaw and in which x and y are such that x<1, y<1, and y·x, in which Ca, $PO_4$ and/or OH are partly replaced by other metals in the case of Ca, and/or by other anions in the case of $PO_4$ and OH.

According to this embodiment of the invention, in step a), a mixture of powders is prepared including in addition at least one compound chosen from the salts, oxides and hydroxides of the alkaline metals, alkaline-earth metals, silver or other metals, and silicon oxide, the aforesaid mixture being able to form a stoichiometric apatite of formula:

$$Ca_{10}(PO_4)_6(OH)_2 \quad (II)$$

or non-stoichiometric apatite with the formula:

$$Ca_{10-x}V_x(PO_4)_{6-y}(HPO_4)_y(OH)_{2+y-2x} \quad (III)$$

in which V represents a flaw and in which x and y are such that x<1, y<1, and y·x, in which Ca, $PO_4$ and/or OH are partly replaced respectively by other metals and/or by other anions.

For making this mixture, the salts used can be chosen from the phosphates, silicates, citrates, nitrates, carbonates, and halides.

This embodiment of the invention process allows for including cations and anions which have particular value for the planned application within the apatite structure.

If the process is used to produce an apatite ceramic for biological use, it may be useful to include strontium in this structure by preparing a mixture of powders including strontium and calcium phosphate of the formula:

$$Ca_2Sr(PO_4)_2$$

or by replacing one or several of the calcium phosphate compounds used by the analogous strontium phosphate compounds, or by mixed calcium-strontium compounds. The following compounds could be used: $Sr(H_2PO_4)_2$, $Sr(H_2PO_4)_2 \cdot H_2O$, $Sr(HPO_4)$, $Sr(PHO_4) \cdot 2H_2O$, $Sr_3(PO_4)_2$ and $Sr_4(PO_4)_2O$.

The presence of strontium in an apatite ceramic for biological use is valuable because it facilitates bone regeneration.

For biological applications, calcium carbonate can also be added to the powder mixture in order to produce a carbonated apatite which is similar to bone.

A silicon compound chosen from among silicon oxide $SiO_2$, calcium metasilicate $CaSiO_3$, and the metasilicates of other metals can also be added to the mixture to produce a silicated apatite ceramic, i.e. a hydroxyapatite in which the $PO_4$ anions are substituted by $SiO_4$ anions. These silicated apatites can be used for protein fixing.

The invention process can thus provide various materials adapted to the planned application.

The invention process is based on a hydrothermal reaction between the various components of the previously compacted mixture of powders.

In step a) of this process, a mixture of powders which can give a hydroxyapatite of the following formula is prepared:

$$Ca_{10}(PO_4)_6(OH)_2$$

in which the anions and/or cations can be substituted by other cations and anions.

The mixture can be made by grinding the ingredients to a size grading of less than 100 μm.

The ingredients of the mixture are chosen as a function of the composition sought.

To prepare a phosphocalcic hydroxyapatite type apatite ceramic, a mixture of various calcium phosphate compounds is used such as monocalcium phosphate $Ca(H_2PO_4)_2$, hydrated monocalcium phosphate $Ca(H_2PO_4)_2 \cdot H_2O$, bicalcium phosphate anhydride $Ca(HPO_4)$ or dihydrated $Ca(HPO_4) \cdot 2H_2O$, tricalcium phosphate of the α or β variety $Ca_3(PO_4)_2$, and tetracalcium phosphate $Ca_4P_2O_9$ in proportions such that the final composition is that of a hydroxyapatite of the formula:

$$Ca_{10}(PO_4)_6(OH)_2 \quad (II)$$

Mixtures containing at least two phosphate compounds are advantageously used, including one basic compound (tetracalcium phosphate) and one or several acidic compounds (dicalcium or monocalcium phosphate).

Two or more ingredients can be used in each mixture in order to easily adjust the formula of the final apatite ceramic.

Other additives can also be added to the powder mixture in order to give the hydroxyapatite obtained useful characteristics for the planned application.

In the case of apatite ceramics for biological use, it may be valuable to add a mixture of powders of at least one additive chosen from granulates of previously calcinated hydroxyapatite, reinforcement particles which are acceptable from a biological standpoint, radioactive tracers and bioactive additives used in orthopedics or dentistry such as pharmaceutical compounds, bactericide, antibiotic, antibacteria and antimitotic agents, and growth factors, as long as they can withstand temperatures of at least 100° C.

For non-biological uses, other additives may be used, for example additives such as neodymium in traces and europium II or III in traces, for their luminescent properties.

Hydroxyapatite granulates and reinforcement particles improve the mechanical properties of the material. Alumina and nylon particles are examples of reinforcement particles.

The addition of radioactive tracers can also be useful for monitoring the insertion of an implant by scintigraphy. This radioactive tracer could be Tc in the form of Technetium-99 m phosphate for example.

Pharmaceutical compounds such as antibiotic agents which can withstand at least 100° C. and bactericide agents, silver for example, can also be added to the biomaterials.

For other applications, additives such as nylons or Kevlar can also be added to improve mechanical resistance.

After preparation of the mixture of powders possibly including such additives, the mixture is subjected to the compacting step b).

The compacting is done at room temperature, from 15 to 30° C. for example, under a pressure of 100 to 500 MPa, preferably 200 MPa, by means of a hydraulic press after putting the mixture into a mould for example.

In step c), the compacted piece is subjected to a hydrothermal treatment in a sealed chamber in the presence of an aqueous medium brought to a temperature of 100 to 500° C. under a pressure which corresponds to the water vapour pressure at the chosen temperature.

The water vapour pressure in the sealed chamber used for this treatment is preferably from 0.5 to 17 MPa.

This treatment yields a ceramic form through a hydrothermal reaction between the compacted components of the mixture. Pieces with exceptional hardness can thus be obtained because acicular crystals of apatite which condition the cohesion of this material have developed within the massive material.

The hydrothermal treatment can be done in two ways.

According to a first embodiment of the treatment, the compacted piece is totally immersed in the aqueous medium so that it is in contact with the water in the liquid state.

According to a second embodiment of this hydrothermal treatment, preferably used for compacted pieces including compounds which are soluble in aqueous media, the compacted piece is arranged above the liquid medium so that it is only in contact with the water vapour produced within the sealed chamber under the effect of the treatment temperature.

The hydrothermal treatment temperature is between 100 and 500° C., and the duration of this hydrothermal treatment depends in particular on the temperature used, the duration being longer when the temperature is lower. The duration is generally at least 8 hours and can be as long as 60 hours.

The hydrothermal treatment temperature is preferably 150 to 250° C. for a period of about 48 hours.

The aqueous medium used is usually demineralised water, but an aqueous solution containing appropriate additives could also be used.

An aqueous solution of sodium fluoride could be used as the aqueous medium to introduce fluoride ions into the structure of the hydroxyapatite in order to decrease the solubility of the hydroxyapatite. The addition of sodium fluoride to the aqueous medium is particularly suitable for preparation of an apatite ceramic for biological use.

According to a variant of the invention process embodiment, there is an additional step d) of sintering of the compacted piece which was subjected to hydrothermal treatment. This sintering is done at a temperature of at least 1,000° C., for example between 1,000 and 1,300° C.

Highly compacted materials with excellent mechanical properties can thus be obtained.

The invention process is thus very valuable because it can yield various compositions of apatite ceramics depending on the compounds used in the starting mixture. Non-stoichiometric apatites can also be prepared by this process having in particular a Ca/P atomic ratio less than 1.667 by using quantities of components in the mixture such that the overall Ca/P atomic ratio is less than 1.667.

The preparation of non-stoichiometric apatites is of great value because it yields a biocompatible compound which is more soluble than stoichiometric hydroxyapatite. This property can be valuable for manufacturing pieces which can be resorbed and then substituted by bone tissue neoformed by the organism.

Non-stoichiometric apatite can also be obtained by adjusting the duration of the hydrothermal treatment step to obtain an apatite mixed with one of the starting calcium phosphates such as tricalcium phosphate. If the duration of the reaction is such that the reaction is not total, there may be some tricalcium phosphate which remains in the piece which is not transformed into hydroxyapatite by the hydrothermal reaction.

Other characteristics and advantages of the invention will be clearer with a reading of the following examples, given as non-limiting illustrations, with reference to the appended drawing.

DETAILED DESCRIPTION OF EMBODIMENTS

EXAMPLE 1

Preparation of Phosphocalcic Hydroxyapatite

Figure 1:
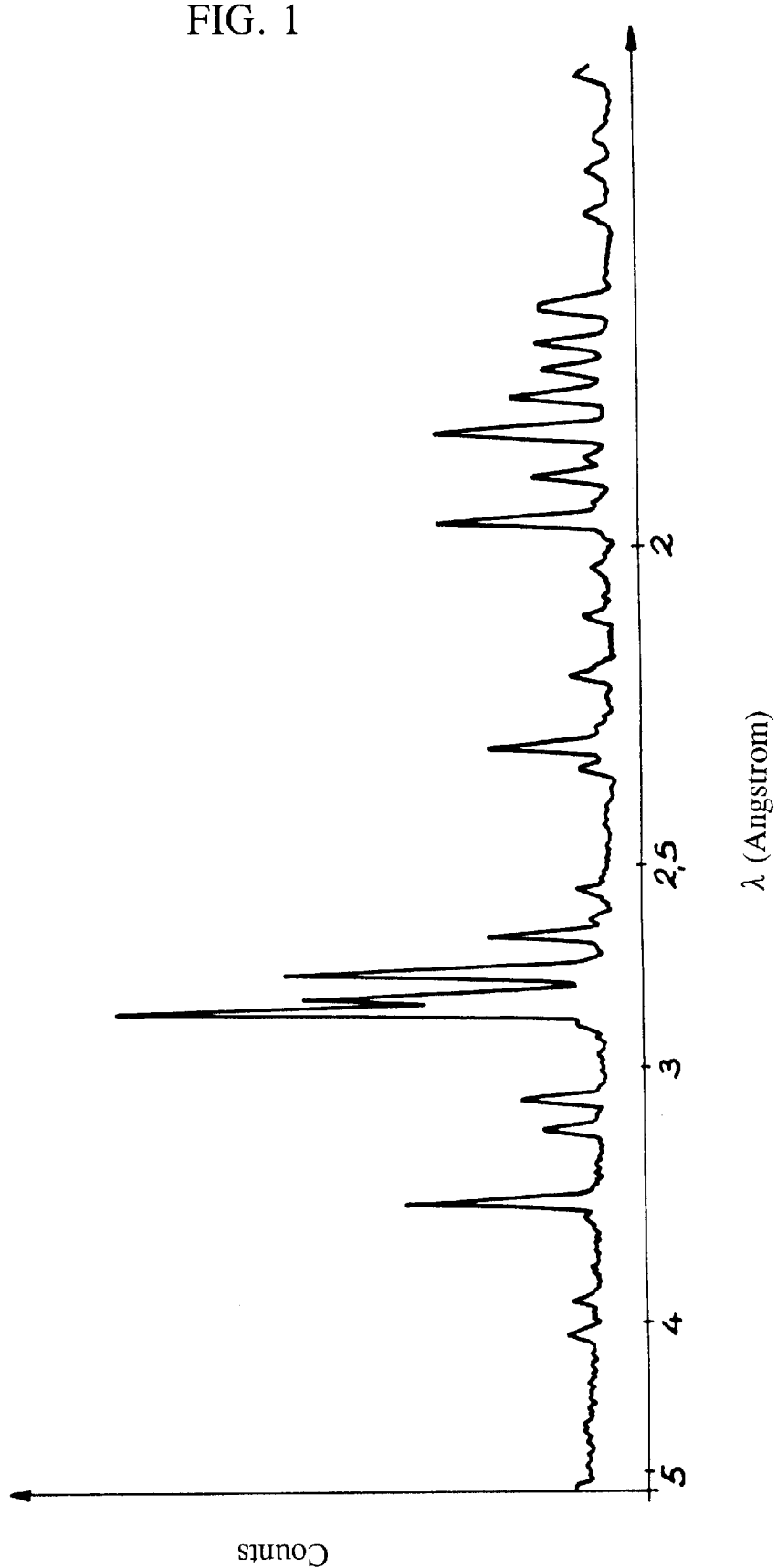
FIG. 1 is a diagram of the X-ray diffraction illustrating the structure of the apatite ceramic obtained in example 1.

In this example, a mixture of powders is first made from the three calcium phosphates which are:

hydrated monocalcium phosphate, $Ca(H_2PO_4)_2 \cdot H_2O$ tricalcium phosphate $Ca_3(PO_4)_2$, and tetracalcium phosphate $Ca_4(PO_4)_2O$.

The proportion of each ingredient is calculated from the following reaction:

a $Ca(H_2PO_4)_2 \cdot H_2O$ + b $Ca_3(PO_4)_2$ + c $Ca_4(PO_4)_2O \rightarrow Ca_{10}(PO_4)_6(OH)_2$ (in the presence of water)

where the coefficients a, b and c are related by the following equation:

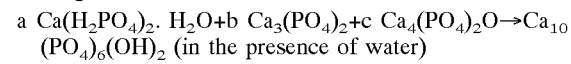

$$b=2-3a, c=1+2a$$

with 0·a·0.67; 0·b·2 and 1·c·2.33.

In this example, the following values are used:

a=0.225 b=1.325, and c=1.45.

After formation of a homogenous mixture by grinding to a size grading of less than 100 μm, the mixture of powders is put in a mould, then it is subjected to compacting in the mould under a pressure of 200 MPa by means of a hydraulic press.

After removal of the compacted piece from the mould, it is put into an autoclave containing demineralised water so that it is totally immersed in the demineralised water. After the closing of the autoclave, it is put into an heated chamber which is brought to 200° C. for a period of 48 hours.

This yields a very well crystallised piece of hydroxyapatite.

FIG. 1 shows the X-ray diffraction diagram for the material thus obtained. The diagram shows that very little tricalcium phosphate remains.

If the time that the mixture remains in the autoclave is increased, this residual tricalcium phosphate is transformed into hydroxyapatite in the aqueous medium.

A electron microscopy scan study revealed the presence of large acicular crystals of calcium hydroxyapatite, thus confirming the very good crystallinity of the product.

The mechanical resistance of this material to compression is close to 100 MPa.

This material can be easily machined and is particularly well suited for bone prosthesis.

EXAMPLE 2

Preparation of Phosphocalcic Hydroxyapatites

In this example, a mixture of phosphates is made as in example 1, then subjected to compacting in the same conditions as in example 1.

After removal of the compacted piece from the mould, it is put into an autoclave containing demineralised water, but it is placed above the water level so that the reaction is in the vapour medium.

The autoclave is closed and put into a heated chamber and brought to a temperature of 200° C. for 48 hours.

At the end of the operation, a material with properties analogous to those of the material in example 1 is obtained.

EXAMPLE 3

Preparation of an Apatite Ceramic Containing Strontium

This example starts with a mixture of powders of hydrated monocalcium phosphate, tetracalcium phosphate and strontium and calcium phosphate $Ca_2Sr(HPO_4)_2$. The proportion of each component is calculated from the following reaction:

$$a\ Ca(HPO_4)_2 \cdot H_2O + b\ Ca_4Sr(PO_4)_2 + c\ Ca_4(PO_4)_2O \rightarrow Ca_9Sr(PO_4)_6(OH)_2$$

with:

a=0.34 b=1 c=1.66.

These ingredients are mixed by grinding, then the mixture of the powders is put into a mould and it is compressed by means of a hydraulic press under pressure of 190 MPa. The compressed piece obtained is then put into an autoclave and covered with demineralised water. The autoclave is closed and the temperature is brought to 200° C., which corresponds to a water vapour pressure of 1.6 MPa, for a period of 72 hours.

This yields a calcium-strontium hydroxyapatite which can be used as a biomaterial, particularly to facilitate bone regeneration.

The material obtained has a resistance to compression of more than 100 MPa.

The invention process is particularly valuable because it yields apatite ceramics with good mechanical properties, particularly for biological use, and allows for introduction of various additives into these ceramics to give them improved mechanical characteristics or other properties.

REFERENCE CITED

Bioceramics, Vol. 10, 1997, pages 75 to 78.

TABLE

Solubility of various calcium phosphates

| NAME | Chemical formula | Ca/P | pKs (at 25° C.) |
|---|---|---|---|
| Tetracalcium Phosphate TTCP | $Ca_4(PO_4)_2O$ | 2 | 40 |
| Hydroxyapatite HAp | $Ca_{10}(PO_4)_6(OH)_2$ | 1.667 | 120 |
| Tricalcium Phosphate •-TCP | •-$Ca_3(PO_4)_2$ | 1.5 | 28.9 |
| Tricalcium Phosphate •-TCP | •-$Ca_3(PO_4)_2$ | 1.5 | 25.5 |
| Octocalcium Phosphate OCP | $Ca_8H_2(PO_4)_6 5H_2O$ | 1.333 | 96.6 |
| Dicalcium Phosphate Dihydrate (Brushite) DCPD | $CaHPO_4 \cdot 2H_2O$ | 1 | 6.60 |
| Dicalcium Phosphate Anhydride (Monetite) DCPA | $CaHPO_4$ | 1 | 6.90 |
| Monocalcium Phosphate Monohydrate MCPM | $Ca(H_2PO_4)_2 \cdot H_2O$ | 0.5 | 2.3 |
| Monocalcium Phosphate MCP | $Ca(HPO_4)_2$ | 0.5 | 2.4 |

What is claimed is:

1. Process for manufacturing an apatite ceramic, including the following steps:
    a) preparing a homogeneous mixture of powders including at least two calcium phosphates chosen from: $Ca(H_2PO_4)_2$, $Ca(H_2PO_4)_2 \cdot H_2O$, $Ca(HPO_4) \cdot 2H_2O$, $Ca_3(PO_4)_2$ of the α and β variety, and $Ca_4(PO_4)_2O$, in quantities such that the mixture corresponds to a stoichiometric hydroxyapatite of formula:

$$Ca_{10}(PO_4)_6(OH)_2 \qquad (II);$$

or a non-stoichiometric hydroxyapatite of formula:

$$Ca_{10-x}V_x(PO_4)_{6-y}(HPO_4)_y(OH)_{2+y-2x} \qquad (III)$$

in which V represents a flaw and in which x and y are such that x<1, y<1, and y≦x, having a Ca/P atomic ratio less than 1.667;
    b) compacting the mixture of powders obtained in step a) at room temperature, under a pressure of 100 to 500 MPa, to yield a compacted piece; and
    c) subjecting the compacted piece to hydrothermal treatment in a sealed chamber containing an aqueous medium, at a temperature of 100 to 500° C., for a period of at least 8 hours.

2. Process for manufacturing an apatite ceramic, including the following steps:
    a) preparing a homogeneous mixture of powders including at least two calcium phosphates chosen from: $Ca(H_2PO_4)_2$, $Ca(H_2PO_4)_2 \cdot H_2O$, $Ca(HPO_4) \cdot 2H_2O$, $Ca_3(PO_4)_2$, of the α and β variety, and $Ca_4(PO_4)_2O$, and optionally containing at least one compound chosen from salts, oxides, hydroxides of alkaline metals, alkaline earth metals, silver and other metals, and $SiO_2$ in quantities such that the mixture is able to form stoichiometric hydroxyapatite of formula:

$$Ca_{10}(PO_4)_6(OH)_2 \qquad (II);$$

or a non-stoichiometric hydroxyapatite of formula:

$$Ca_{10-x}V_x(PO_4)_{6-y}(HPO_4)_y(OH)_{2+y-2x} \qquad (III)$$

in which V represents a flaw and in which x and y are such that x<1, y<1, and y≦x, having a Ca/P atomic ratio less than 1.667;
       wherein in formula II and formula III; Ca is optionally partly replaced by alkaline metals, other alkaline earth metals, silver and other metals and $PO_4$ and/or OH groups are optionally replaced with other anions;
    b) compacting the mixture of powders obtained in step a) at room temperature, under a pressure of 100 to 500 MPa, to yield a compacted piece; and c) subjecting the compacted piece to hydrothermal treatment in a sealed chamber containing an aqueous medium, at a temperature of 100 to 500° C., for a period of at least 8 hours.

3. Process according to claim 2, in which, in step a), a mixture of powders further including at least one compound chosen from salts, oxides and hydroxides of alkaline metals, alkaline-earth metals, silver or other metals, and silicon oxide is prepared, the aforesaid mixture being able to form a stoichiometric apatite of formula:

$$Ca_{10}(PO_4)_6(OH)_2$$

or a non-stoichiometric apatite of formula:

$$Ca_{10-x}V_x(PO_4)_{6-y}(HPO_4)_y(OH)_{2+y-2x} \quad (III)$$

in which V represents a flaw and in which x and y are such that x<1, y<1, and y≦x, in which Ca is partly replaced with other metals and $PO_4$ and/or OH are respectively partly replaced by other anions.

4. Process according to claim 3, in which the salts are chosen from among the phosphates, silicates, citrates, nitrates, carbonates and halides.

5. Process according to claim 4, for the preparation of an apatite ceramic for biological use, in which the mixture of powders includes strontium and calcium phosphate of formula:

$$Ca_2Sr(PO_4)_2$$

or a strontium compound of formula: $Sr(H_2PO_4)_2$, $Sr(H_2PO_4)_2.H_2O$, $Sr(HPO_4)$, $Sr(PHO_4).2H_2O$, $Sr_3(PO_4)_2$ and $Sr_4(PO_4)_2O$.

6. Process according to claim 3, for the preparation of an apatite ceramic for biological use, in which the mixture of powders includes calcium carbonate.

7. Process according to claim 3, for the preparation of an apatite ceramic for biological use, in which the mixture of powders includes a silicon compound chosen from silicon oxide "$SiO_2$", calcium metasilicate "$CaSiO_3$", and the metasilicates of other metals.

8. Process according claim 2, which also includes an additional step:
d) of sintering at a temperature of at least 1,000° C., of the compacted piece subjected to hydrothermal treatment obtained in step c).

9. Process according to claim 2, in which, in step a), the mixture of powders is prepared by grinding said mixture.

10. Process according to claim 2, in which, in step c), the compacted piece is totally immersed in the aqueous medium.

11. Process according to claim 2, in which, in step c), the compacted piece is arranged above the aqueous medium.

12. Process according to claim 2, in which the water vapor pressure in the sealed chamber used in step c) is from 0.5 to 17 Mpa.

13. Process according to claim 2, in which the duration of hydrothermal treatment is from 8 to 60 hours.

14. Process according to claim 2, in which the aqueous medium is demineralized water.

15. Process according to claim 2, for the preparation of an apatite ceramic for biological use, in which at least one additive chosen from granulates of previously calcinated hydroxyapatite, reinforcement particles which are acceptable from a biological standpoint, radioactive tracers, bioactive agents chose from pharmaceutical compounds, bactericide, antibiotic, antibacterial and antimitotic agents, and growth factors, is added to the powder mixture.

16. Process according to claim 15, in which the radioactive tracer is Technetium-99m Phosphate.

17. Process according to claim 15, in which the bactericide agent is silver.

18. Process according to claim 15, in which the aqueous medium used in step c) includes sodium fluoride.

19. Process according to claim 2, for the preparation of an apatite ceramic for biological use, in which the aqueous medium used in step c) includes sodium fluoride.

20. Process according to claim 2, in which the mixture of powders includes at least one of a luminous additive and an additive to improve mechanical resistance.

* * * * *